(12) United States Patent
Uratani et al.

(10) Patent No.: US 9,863,851 B2
(45) Date of Patent: Jan. 9, 2018

(54) EXHAUST GAS MEASURING INFORMATION PROCESSING APPARATUS, EXHAUST GAS MEASURING SYSTEM, AND RECORDING MEDIUM

(71) Applicant: HORIBA, Ltd., Kyoto (JP)

(72) Inventors: Katsumi Uratani, Kyoto (JP); Shun Fukami, Kyoto (JP)

(73) Assignee: Horiba, Ltd., Kyoto (JP)

( * ) Notice: Subject to any disclaimer, the term of this patent is extended or adjusted under 35 U.S.C. 154(b) by 230 days.

(21) Appl. No.: 14/824,426

(22) Filed: Aug. 12, 2015

(65) Prior Publication Data

US 2016/0047718 A1 Feb. 18, 2016

(30) Foreign Application Priority Data

Aug. 12, 2014 (JP) .................................. 2014-164603

(51) Int. Cl.
*G01M 15/10* (2006.01)
*F01N 13/00* (2010.01)
(Continued)

(52) U.S. Cl.
CPC ......... *G01M 15/102* (2013.01); *F01N 13/008* (2013.01); *G01F 1/46* (2013.01);
(Continued)

(58) Field of Classification Search
USPC ............... 73/114.69, 114.71, 114.72, 114.73, 73/114.74
See application file for complete search history.

(56) References Cited

U.S. PATENT DOCUMENTS 7,124,621 B2 * 10/2006 Nevius ...................... G01F 1/66
702/100
2008/0148811 A1 * 6/2008 Ruth ..................... G01M 15/05
73/23.21

(Continued)

FOREIGN PATENT DOCUMENTS

JP 2010-139340 A 6/2010
JP 2014-020808 A 2/2014

OTHER PUBLICATIONS

EESR dated Jan. 18, 2016 issued for European Patent Application No. 15 179 969.9, 7 pgs.

*Primary Examiner* — Eric S McCall
(74) *Attorney, Agent, or Firm* — Brooks Kushman P.C.

(57) ABSTRACT

An exhaust gas measuring information processing apparatus of the present invention detects troubles etc. of a flow sensor during a flow rate measurement and performs predetermined processing relevant to maintenance and check of the flow sensor. The exhaust gas measuring information processing apparatus includes a reception circuit that receives a flow rate measurement signal indicating a flow rate measurement value of exhaust gas flowing through an exhaust gas tube of an internal combustion engine and an operational state signal indicating an operational state of the internal combustion engine, and a processing executing circuit that executes predetermined processing relevant to maintenance and check of the flow sensor that outputs the flow rate measurement signal when a predetermined correlation is not satisfied between an index value for the operational state indicated by the operational state signal and the flow rate measurement value indicated by the flow rate measurement signal.

11 Claims, 6 Drawing Sheets

(51) Int. Cl.
*G01N 33/00* (2006.01)
*G01F 1/46* (2006.01)
*G01N 1/22* (2006.01)
*G01N 21/3504* (2014.01)
*G01N 21/76* (2006.01)

(52) U.S. Cl.
CPC ......... *G01N 1/2252* (2013.01); *G01N 33/004* (2013.01); *G01N 21/3504* (2013.01); *G01N 21/766* (2013.01)

(56) References Cited

U.S. PATENT DOCUMENTS

| | | | |
|---|---|---|---|
| 2008/0295489 A1* | 12/2008 | Elfvik | F01N 3/2066 60/277 |
| 2011/0166768 A1* | 7/2011 | Yamaoka | F02D 41/0245 701/103 |
| 2012/0160009 A1 | 6/2012 | Asami et al. | |
| 2013/0136656 A1 | 5/2013 | Okada et al. | |
| 2013/0152583 A1* | 6/2013 | Uesugi | F01D 17/165 60/608 |
| 2014/0338540 A1* | 11/2014 | Yoshimura | G01N 1/2252 96/413 |
| 2014/0345373 A1* | 11/2014 | Akita | G01F 9/00 73/114.52 |
| 2015/0046101 A1* | 2/2015 | Akita | F02D 41/1445 702/45 |
| 2015/0218991 A1* | 8/2015 | Chavannavar | F01N 3/208 423/239.1 |
| 2015/0226596 A1* | 8/2015 | Baumeister | G01F 25/0007 73/1.16 |
| 2015/0354428 A1* | 12/2015 | Sun | F01N 9/007 701/102 |

* cited by examiner

EXHAUST GAS MEASURING INFORMATION PROCESSING APPARATUS, EXHAUST GAS MEASURING SYSTEM, AND RECORDING MEDIUM

CROSS-REFERENCE TO RELATED APPLICATIONS

This application claims priority to JP Application No. 2014-164603, filed Aug. 12, 2014, the disclosure of which is incorporated in its entirety by reference herein.

TECHNICAL FIELD

The present disclosure relates to an exhaust gas measuring information processing apparatus, an exhaust gas measuring system, and an exhaust gas measuring program recording medium, for conducting a predetermined process relevant to checking and maintenance of a flow sensor.

BACKGROUND ART

Pitot tube type flowmeters are commonly used for measuring a flow rate of exhaust gas of an internal combustion engine, for example, as illustrated in Japanese Laid-open Patent Publication No. 2014-20808. The pitot tube type flowmeter includes a dynamic pressure tube that measures a dynamic pressure of exhaust gas flowing through an exhaust gas tube, a static pressure tube that measures a static pressure of exhaust gas flowing through the exhaust gas tube, and a differential pressure gauge that measures a differential pressure between dynamic pressure and static pressure. Further, the pitot tube type flowmeter calculates a current speed on the basis of the differential pressure and multiplies the current speed by a cross-section area of the exhaust gas tube to measure the flow rate. On the dynamic pressure tube, measuring holes for introducing the exhaust gas are provided in a facing direction to a flowing direction of the exhaust gas, and on the static pressure tube, measuring holes are provided in an opposing direction to the flowing direction of the exhaust gas.

From a standpoint of a configuration of the pitot tube type flowmeter, when this dynamic pressure tube is clogged with foreign materials, the dynamic pressure is not correctly measured and the flow rate of the exhaust gas is not correctly measured. To deal with the above, conventionally, irrespective of whether or not the dynamic pressure tube is clogged with foreign materials, the dynamic pressure tube is forcibly purged at each predetermined timing to secure correct operations of the pitot tube type flowmeter.

Also in flow sensors other than the pitot tube type flowmeter, when troubles occur in the flow sensor, an exhaust gas flow rate of the internal combustion engine is not correctly measured. Therefore, it is necessary to detect the troubles in the flow sensor and secure normal operations.

However, with the configuration as described above where the dynamic pressure tube is forcibly purged at each predetermined timing, there is a problem that it is difficult to purge the dynamic pressure tube at appropriate timing, so that the dynamic pressure tube cannot be immediately purged to remove the foreign materials when clogged with foreign materials. In addition, in the case in which the dynamic pressure tube is forcibly purged, there is a problem that, even if not clogged with foreign materials, the dynamic pressure tube is purged, and therefore it is excessively purged.

SUMMARY OF INVENTION

Technical Problem

In view of the foregoing, to solve the above-described problem, it is an object of the present invention to perform processing for detecting troubles etc. of a flow sensor during a flow rate measurement of exhaust gas of an internal combustion engine and normalizing the flow sensor at appropriate timing.

Solution to Problem

Specifically, an exhaust gas measuring information processing apparatus according to the present invention includes a reception circuit that receives a flow rate measurement signal indicating a flow rate measurement value of exhaust gas flowing through an exhaust gas tube of an internal combustion engine and an operational state signal indicating an operational state of the internal combustion engine, and a processing executing circuit that executes predetermined processing relevant to maintenance and check of a flow sensor that outputs the flow rate measurement signal when a predetermined correlation is not satisfied between an index value for the operational state indicated by the operational state signal and the flow rate measurement value indicated by the flow rate measurement signal.

Further, an exhaust gas measuring system according to the present invention includes the exhaust gas measuring information processing apparatus, the flow sensor that measures a flow rate of the exhaust gas flowing through the exhaust gas tube of the internal combustion engine and outputs the flow rate measurement signal indicating the flow rate measurement value, and an operational state detecting sensor that detects the operational state of the internal combustion engine and outputs the operational state signal indicating the detected operational state.

Further, a program according to the present invention causes the exhaust gas measuring information processing apparatus to function as the reception circuit that receives the flow rate measurement signal indicating the flow rate measurement value of the exhaust gas flowing through the exhaust gas tube of the internal combustion engine and the operational state signal indicating the operational state of the internal combustion engine, and the processing executing circuit that executes the predetermined processing relevant to the maintenance and check of the flow sensor that outputs the flow rate measurement signal when the predetermined correlation is not satisfied between the index value for the operational state indicated by the operational state signal and the flow rate measurement value indicated by the flow rate measurement signal.

According to the above-described exhaust gas measuring information processing apparatus, exhaust gas measuring system and exhaust gas measuring program, when the predetermined correlation is not satisfied between the index value for the operational state indicated by the operational state signal at the time in which the internal combustion engine is under operation, namely, at the time in which the exhaust gas should flow, and the flow rate measurement value indicated by the flow rate measurement signal during the measurement of the exhaust gas flow rate of the internal combustion engine, it is possible to determine that the predetermined correlation is not satisfied due to troubles with the flow sensor. The predetermined correlation indicates that when the internal combustion engine is under operation, the flow rate measurement value increases above the predetermined value or decreases below the predetermined value in accordance with a change in the increase or decrease of the index value.

When the flow rate measurement value measured by the flow sensor does not satisfy the predetermined value, for example, if the flow rate measurement value is zero, troubles occur in the flow sensor, and as a result, the predetermined processing relevant to the maintenance and check of the flow sensor is performed. Therefore, the predetermined processing is performed at appropriate timing such as at the time at which the troubles occur, and further, the predetermined processing is not forcibly performed, but rather unnecessary processing is avoided.

One specific example where it is recognized that the predetermined correlation is not satisfied, is the case in which it is determined that the internal combustion engine is under operation, on the basis of the index value for the operational state which is indicated by the operational state signal, and the flow rate measurement value indicated by the flow rate measurement signal is less than the predetermined value.

The predetermined processing relevant to the maintenance and check of the flow sensor includes processing steps such as alerting an operator to perform maintenance and check, in addition to the ordering by the processing executing circuit to other devices to perform maintenance and check operation.

For example, as a specific aspect of the predetermined processing, an abnormality in the flow sensor is reported to the operator via a screen or by sound.

In particular, when the flow sensor includes a sensor main body and a conversion circuit that converts an output signal from the sensor main body into the flow rate measurement signal, and the sensor main body includes an exhaust gas introduction tube which is attached to the exhaust gas tube and into which the exhaust gas is introduced, the abnormality is caused in many cases due to clogging of the exhaust gas introduction tube. Therefore, it is preferable that a message "purge is necessary" be displayed as an abnormality report.

Preferably, in the processing executing circuit, it is sufficient to just start the purge operation for the exhaust gas introduction tube as the predetermined processing at timing when the predetermined correlation is not satisfied. According to this arrangement, it is possible to purge the exhaust gas introduction tube automatically, thereby enabling to save power.

As a specific aspect in which existing devices are used as far as possible to realize a simplified configuration without providing a dedicated sensor, there is a case in which the operational state detecting sensor that outputs the operational state signal, detects as the index value, a rotation speed of the internal combustion engine, or an intake air flow rate of the internal combustion engine, or a fuel consumption of the internal combustion engine, or a concentration of a predetermined component contained in the exhaust gas, and the processing executing circuit determines that the internal combustion engine is in an operational state when the index value is more than the predetermined value.

As the operational state detecting sensor, an engine rotational speed sensor previously mounted on a vehicle, a $CO_2$ concentration meter mounted on the exhaust gas measuring system, or the like can be used. Therefore, the quantity of dedicated devices or dedicated processes for a diagnosis of the flow sensor can be reduced. For example, the process flowing a standard gas whose flow rate changes in a predetermined pattern in order to check an output of the flow sensor, can be reduced. Or, alternatively, the dedicated devices required for processing a flowing a standard gas whose flow rate changes in a predetermined pattern in order to check an output of the flow sensor, can be reduced. This makes it possible to shorten the time it takes to conduct the whole exhaust gas measurement process including preparatory work, and work conducted between, and after measurement. Furthermore, it is possible to simplify the configuration of the exhaust gas measuring system.

When the exhaust gas measuring system is a vehicle-mounted type exhaust gas measuring system further including a concentration measuring sensor that measures the predetermined component concentration in the exhaust gas and a component exhaust amount calculation circuit that calculates an exhaust amount of the predetermined component on the basis of a product of measurement concentration of the predetermined component measured by the concentration measuring sensor and the flow rate measurement value measured by the flow sensor, effects of the present invention are exerted more significantly.

Specifically, the vehicle-mounted type exhaust gas measuring system is used for a vehicle that travels on a road rather than on a test bench such as a chassis dynamometer. Such a road traveling test may be performed for several hours. Further, since the road traveling test may be performed only by a vehicle driver, it is difficult to always monitor all measurement data compared with a test on the test bench. In the case when clogging, or other complication, occurs in the flow sensor during the above road traveling test, but the road traveling test is continued without being aware of the clogging, or other complication, data recorded after trouble has occurred in the flow sensor becomes wasted, and the time spent on the travel is wasted as well.

In contrast to the above, according to the present exhaust gas measuring system, it is possible to find out the abnormality of the flow sensor in real time while the vehicle is traveling, as described above, and to take action to normalize the situation. As a result, it is possible to eliminate the wasted test data and travel time by interrupting the road traveling test on the spot and removing as much as possible of the invalid data from the time that the vehicle was traveled with the clogging, or other complication, and then normalizing the situation with appropriate actions.

As one specific aspect of the exhaust gas measuring system, the operational state detecting sensor is a $CO_2$ sensor that measures concentration of $CO_2$ in the exhaust gas, and the processing executing circuit recognizes the measurement concentration of the $CO_2$ as the index value for the operational state, and determines that the internal combustion engine is under operation in the case when the index value is more than the predetermined value.

In particular, when determining the operational state based on a component of the exhaust gas, it is preferable to use $CO_2$ concentration. $CO_2$ is surely contained in the exhaust gas, and $CO_2$ is hardly influenced by catalysts and other potential interferences that may be present along the path of the exhaust gas tube. Therefore, when $CO_2$ is detected, it can be reliably determined that the exhaust gas is flowing and the internal combustion engine is under operation.

Advantageous Effects of Invention

According to the present invention having the above-described configuration, when the predetermined correlation is not satisfied between the index value for the operational state indicating that the internal combustion engine is under operation, and the flow rate measurement value indicated by the flow rate measurement signal during the flow rate measurement of the exhaust gas of the internal combustion engine, it is considered that a complication has occurred in the flow sensor, and consequently predetermined processing relevant to the maintenance and check of the flow sensor is performed. Furthermore, the predetermined processing is performed at the most appropriate timing such, which is the timing at which a complication occurs.

DESCRIPTION OF THE EMBODIMENTS

Hereinafter, one embodiment of an exhaust gas measuring information processing apparatus and an exhaust gas measuring system according to the present invention will be described with reference to the accompanying drawings.

Figure 1:
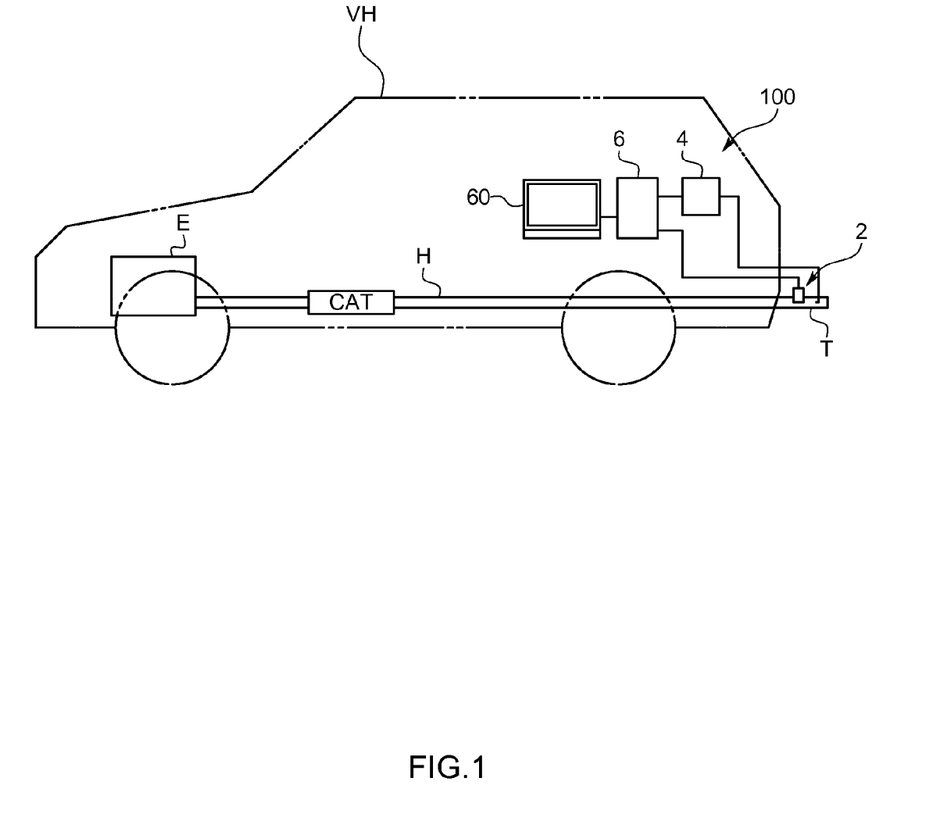
FIG. 1 is a schematic diagram illustrating a configuration of a vehicle-mounted type exhaust gas measuring system according to the present embodiment.

As illustrated in FIG. 1, the exhaust gas measuring system 100 of the present embodiment is mounted on a vehicle VH, measures components of exhaust gas in a road traveling test, and measures fuel consumption. Further, the exhaust gas measuring system 100 includes a flow sensor 2 that measures a flow rate of the exhaust gas flowing through an exhaust gas tube H connected to an internal combustion engine E, an analyzer 4 that collects a part of the exhaust gas flowing through the exhaust gas tube H and analyzes $CO_2$, and an exhaust gas measuring information processing apparatus (hereinafter, referred to as an "information processing apparatus 6") that receives a flow rate measurement signal output from the flow sensor 2 and an operational state signal output from the analyzer 4, and reports information necessary for a normalizing action of the flow sensor 2. To the exhaust gas tube H, a catalyst CAT for purging the exhaust gas is attached between the internal combustion engine E and an end T that exhausts the exhaust gas to the outside.

Figure 2:
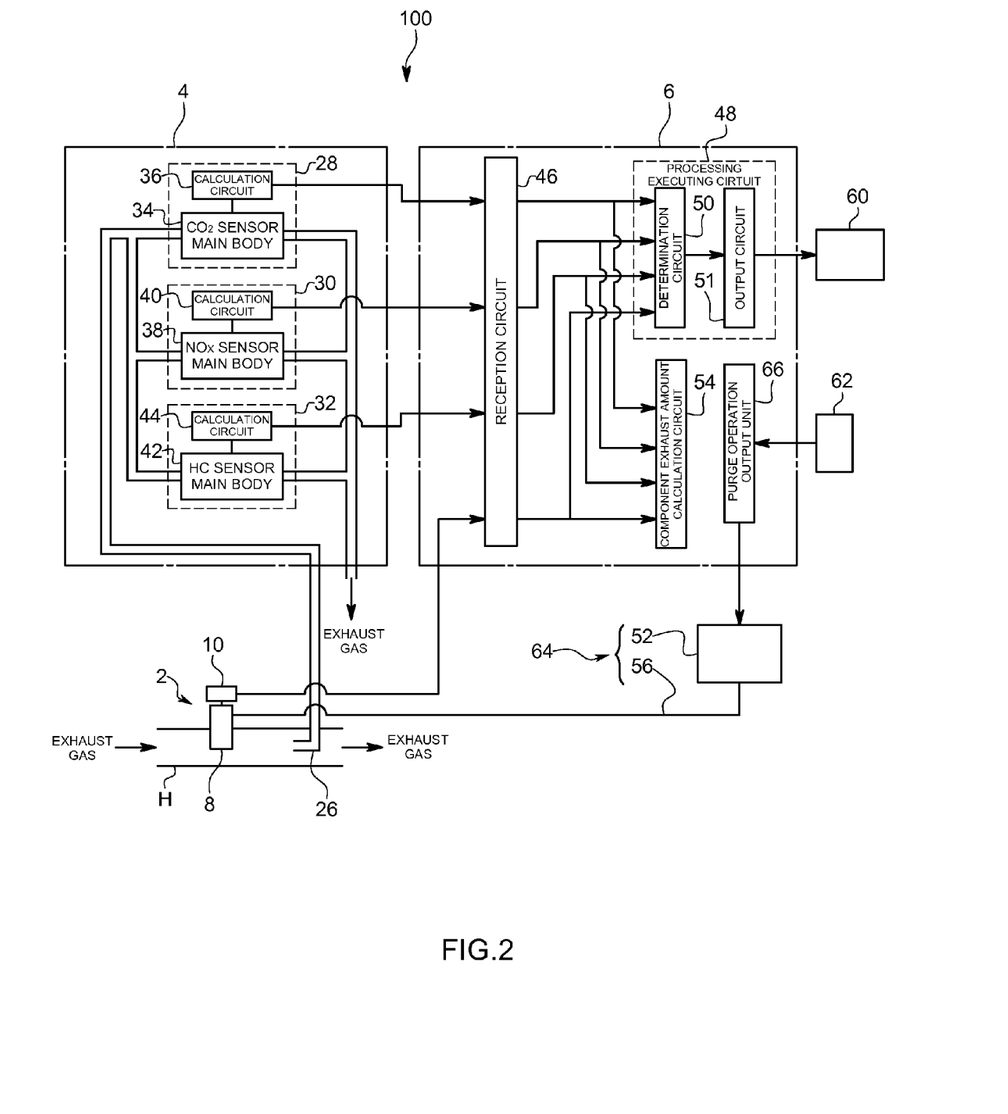
FIG. 2 is a schematic diagram illustrating a specific configuration of the exhaust gas measuring system according to the present embodiment.
Figure 3:
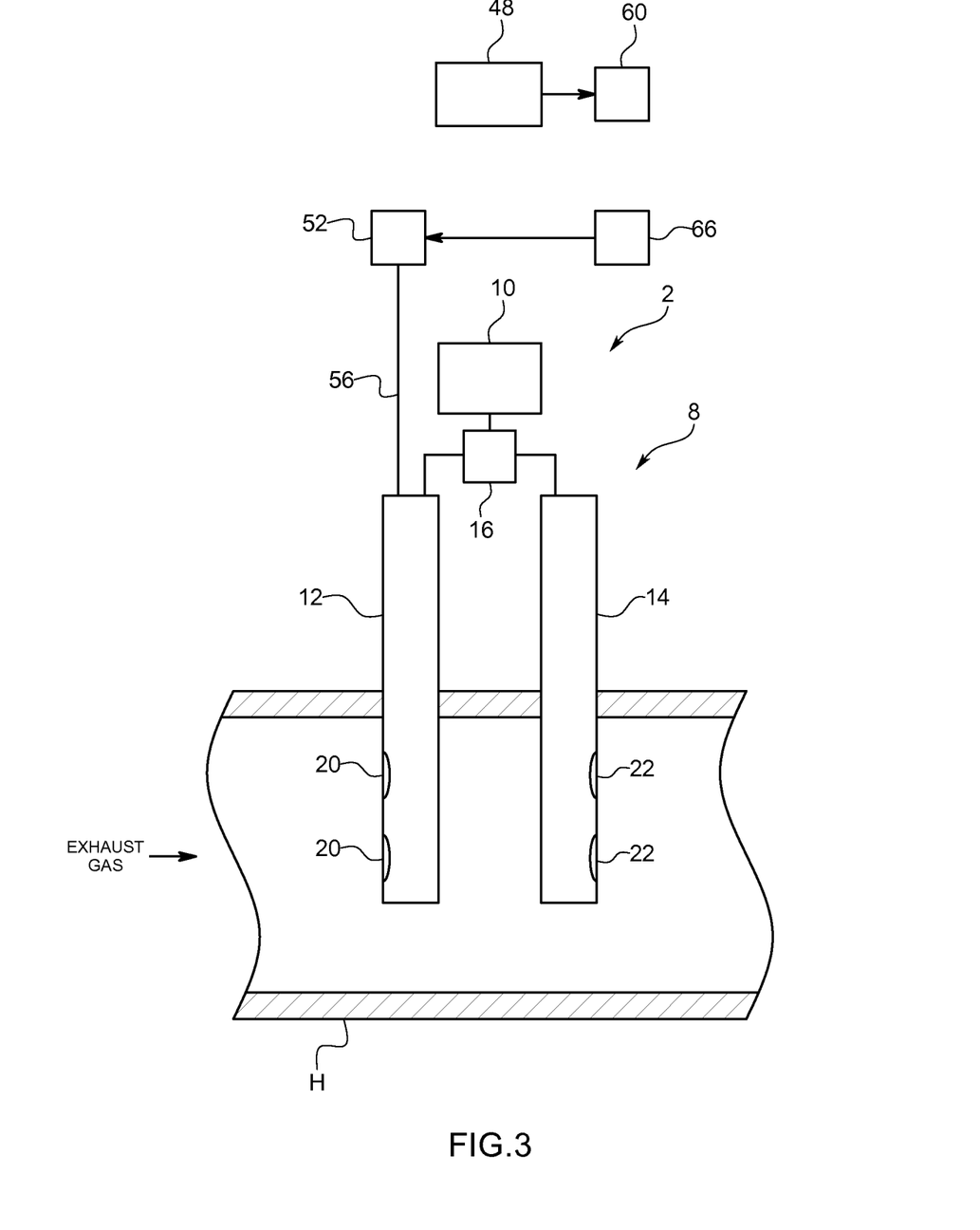
FIG. 3 is a schematic diagram illustrating a specific configuration of a flow sensor according to the present embodiment.

First, the flow sensor 2 will be described with reference to FIGS. 2 and 3. The flow sensor 2 includes a sensor main body 8 that measures a current speed of the exhaust gas and a conversion circuit 10 that converts the current speed into the flow rate.

The sensor main body 8 is the pitot tube type flowmeter including a dynamic pressure tube 12 and a static pressure tube 14 serving as an exhaust gas introduction tube, and a differential pressure gauge 16 that is disposed between the dynamic pressure tube 12 and the static pressure tube 14.

At the end T of the exhaust gas tube H, the dynamic pressure tube 12 and the static pressure tube 14 are inserted into the inside of the exhaust gas tube H from an upper part of a radial direction. The dynamic pressure tube 12 is arranged on the upstream side in a flow direction of the exhaust gas and the static pressure tube 14 is arranged on the downstream side in a flow direction of the exhaust gas while being spaced apart by a specified distance. Two dynamic pressure measuring holes 20 that are opened to face the flowing direction of the exhaust gas flowing through the exhaust gas tube H are vertically formed on a surface of the dynamic pressure tube 12, and the exhaust gas is introduced into the dynamic pressure tube 12 from the dynamic pressure measuring holes 20. Two static pressure measuring holes 22 that are opened to oppose the flowing direction are vertically formed on a surface of the static pressure tube 14.

The differential pressure gauge 16 includes pressure sensors, which are respectively connected to the dynamic pressure tube 12 and the static pressure tube 14 via a capillary tube. The differential pressure gauge 16 measures a differential pressure generated between the dynamic pressure tube 12 and the static pressure tube 14, and outputs an output signal indicating a value of the differential pressure to the conversion circuit 10.

The conversion circuit 10 converts the output signal from the differential pressure gauge 16 into a flow rate measurement signal. That is, the conversion circuit 10 is configured so as to calculate a current speed of the exhaust gas from a differential pressure value obtained on the basis of the output signal, multiply the current speed by a cross-section area of the exhaust gas tube H in which the dynamic pressure tube 12 and the static pressure tube 14 are arranged to obtain a flow rate measurement value, and output the flow rate measurement signal indicating the flow rate measurement value.

Next, the analyzer 4 will be described. The analyzer 4 includes a $CO_2$ sensor 28 serving as an operational state detecting sensor of the internal combustion engine, a $NO_x$ sensor 30, and an HC (hydrocarbon) sensor 32.

The $CO_2$ sensor 28 measures concentration of carbon dioxide contained in the exhaust gas by a nondispersive infrared absorption (NDIR) method. Further, the $CO_2$ sensor 28 includes a $CO_2$ sensor main body 34 that detects the concentration of the carbon dioxide and a calculation circuit 36 that calculates the $CO_2$ concentration by the use of a value of an output signal output by the $CO_2$ sensor main body 34.

The $NO_x$ sensor 30 measures concentration of $NO_x$ contained in the exhaust gas by a chemiluminescence method. Further, the $NO_x$ sensor 30 includes a $NO_x$ sensor main body 38 that detects the concentration of the $NO_x$ and a calculation circuit 40 that calculates the $NO_x$ concentration by the use of a value of an output signal output by the $NO_x$ sensor main body 38.

The HC sensor 32 measures concentration of hydrocarbon contained in the exhaust gas by a hydrogen flame ionization (FID) method. Further, the HC sensor 32 includes an HC sensor main body 42 that detects hydrocarbon concentration and a calculation circuit 44 that calculates the hydrocarbon concentration by the use of a value of an output signal output by the HC sensor main body 42.

As the operational state detecting sensors, it is possible to use the $CO_2$ concentration meter or the like that is mounted on the exhaust gas measuring system 100.

The exhaust gas measuring system 100 is configured such that a part of the exhaust gas flowing through the exhaust gas tube H is introduced into the sensors 28, 30, and 32 from an exhaust gas introduction probe 26 that is installed on the end T of the exhaust gas tube H. The exhaust gas measuring system 100 is also configured so as to exhaust the exhaust gas after being used in each of the sensors 28, 30, and 32 to the outside of the analyzer 4.

In the present embodiment, the $CO_2$ sensor 28 is used as the operational state detecting sensor among the above sensors.

Next, the information processing apparatus 6 will be described. The information processing apparatus 6 includes a CPU, a memory, an A/D converter, communication ports, and the like (not illustrated). The information processing apparatus 6 is configured to exhibit functions as a reception circuit 46, a component exhaust amount calculation circuit 54, a processing executing circuit 48, a purge operation output unit 66, and the like, which will be described later, by operating the CPU or peripheral devices on the basis of programs stored in the memory.

The reception circuit 46 receives the flow rate measurement signal output from the flow sensor 2 and a $CO_2$ concentration measurement signal output from the $CO_2$ sensor 28 of the analyzer 4 as the operational state signal indicating an operational state of the internal combustion engine E.

The component exhaust amount calculation circuit 54 calculates the exhaust amount of each component in the exhaust gas such as $CO_2$, $NO_X$ and HC on the basis of products of concentration of each component in the exhaust gas and the flow rate measurement values measured by the flow sensor 2, and stores the exhaust amount of each component in the test travel in the memory for calculation of the fuel consumption, and the like.

The processing executing circuit 48 includes: a determination circuit 50 which determines whether or not the internal combustion engine E is under operation on the basis of a value indicated by the operational state signal received by the reception circuit 46, namely, $CO_2$ measurement concentration that is the index value indicating the operational state and which also determines whether or not the flow rate measurement value indicated by the flow rate measurement signal from the flow sensor 2 is less than a predetermined value; and an output circuit 51 which indicates the message "purge is necessary" to a display 60 as predetermined processing relevant to maintenance and check of the flow sensor 2 when the internal combustion engine E is under operation and the flow rate measurement value is less than the predetermined value. Here, the determination circuit 50 recognizes a state in which the flow rate measurement value is less than the predetermined value when the internal combustion engine E is under operation as a state in which a predetermined correlation is not satisfied.

The fact that the flow rate measurement value is less than the predetermined value indicates that a state in which the flow rate measurement value is less than the predetermined value occurs more than once during a fixed period of time, or the state continues for the fixed period of time. The predetermined value is the flow rate measurement value indicated by the flow rate measurement signal from the flow sensor 2, which is equal to or less than a flow rate value during idling of the internal combustion engine E. When the flow rate measurement value measured by the flow sensor 2 is less than the predetermined value, abnormality is caused in many cases due to the fact that the dynamic pressure measuring holes 20 of the dynamic pressure tube 12 are clogged with foreign materials contained in the exhaust gas. Accordingly, it is preferable to indicate the message "purge is necessary" on the display 60 as an abnormality report.

The purge operation output unit 66 receives a purge operation start signal which is input by an operator who has seen the display 60 by the use of an external input device 62 such as a purge button, a keyboard, or a mouse, and outputs the purge operation start signal to a purge device 64.

The purge device 64 includes a purge device main body 52 including a compressor, and further includes a capillary tube 56 for connecting the purge device main body 52 and the dynamic pressure tube 12 of the flow sensor 2. When the purge device 64 receives the purge operation start signal output from the purge operation output unit 66, the compressor operates, and gas such as air is pumped into the dynamic pressure tube 12 through the capillary tube 56. As a result, the purge device 64 removes foreign materials with which the dynamic pressure measuring holes 20 are clogged.

Next, one example of operations of the exhaust gas measuring system 100 will be described with reference to FIGS. 2 to 4. FIG. 2 is a schematic diagram illustrating a configuration of the exhaust gas measuring system 100, FIG. 3 is a schematic diagram illustrating a configuration of the flow sensor 2, and FIG. 4 is a graph showing various flow rate measurement values of the exhaust gas indicated by the flow sensor 2.

When the road traveling test is started, the exhaust gas measuring system 100 starts a flow rate measurement of the exhaust gas with use of the flow sensor 2 and a measurement of $CO_2$ concentration with use of the $CO_2$ sensor 28 of the analyzer 4.

Next, the reception circuit 46 receives, as the operational state signal, the $CO_2$ concentration measurement signal output from the $CO_2$ sensor 28. When a $CO_2$ measurement concentration as the index value indicating the operational state is more than the predetermined value, namely, a value of the $CO_2$ concentration at least generated during the operation, the determination circuit 50 determines that the internal combustion engine E is under operation.

Figure 4:
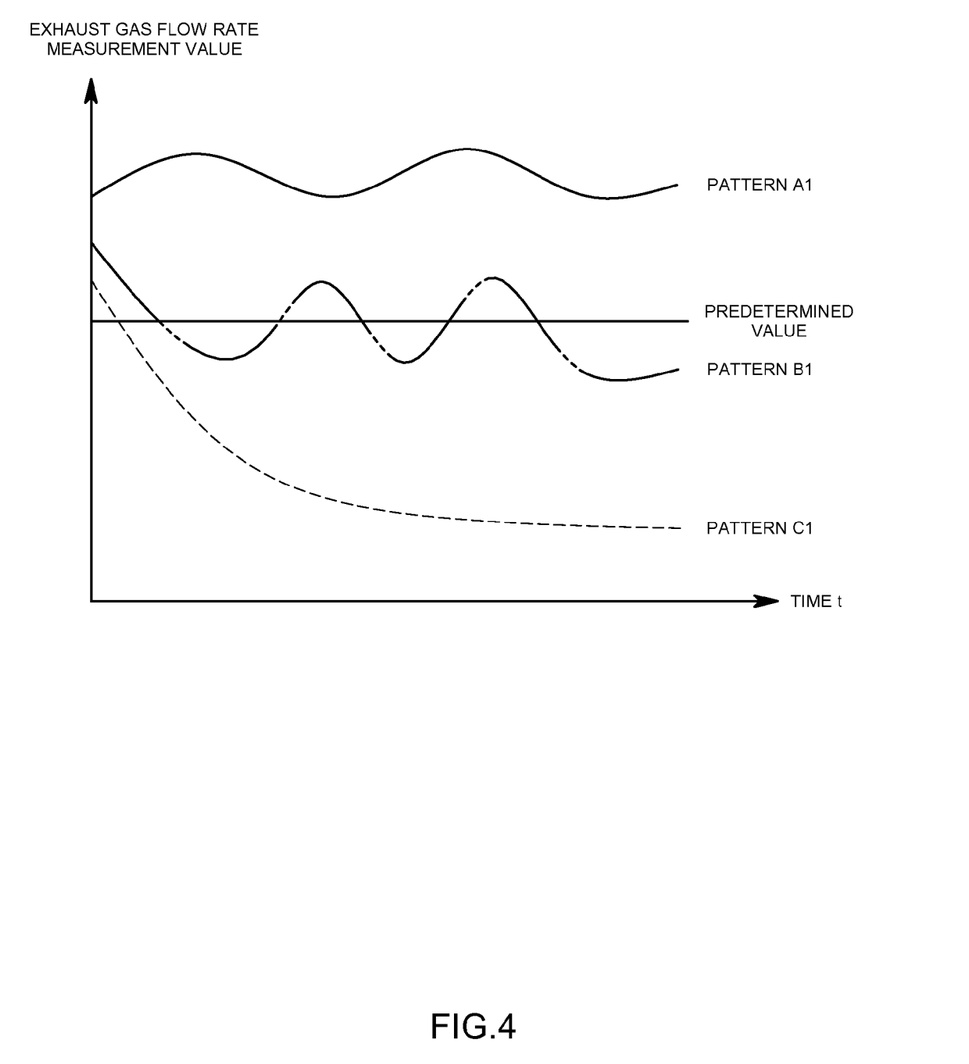
FIG. 4 is a schematic diagram illustrating various states of an exhaust gas flow rate measurement value according to the present embodiment.

Next, in the state in which the internal combustion engine E is under operation, when the flow rate measurement value indicated by the flow sensor 2 is a pattern A1 illustrated in FIG. 4, the determination circuit 50 does not determine that the flow rate measurement value is less than the predetermined value, but the predetermined correlation is satisfied. In this case, a message "purge is necessary" are not displayed on the display 60 and the flow rate measurement is continued.

On the other hand, when the flow rate measurement value indicated by the flow sensor 2 is a pattern B1 or C1 illustrated in FIG. 4, specifically, in the case of a state (pattern B1) in which the flow rate measurement value becomes less than the predetermined value more than once during the fixed period, or a state (pattern C1) in which it is continued for the fixed period that the flow rate measurement value is less than the predetermined value, the determination circuit 50 determines that the flow rate measurement value is less than the predetermined value. The determination circuit 50 further determines that the predetermined correlation is not satisfied, and the output circuit 51 displays the message "purge is necessary" on the display 60.

When the operator who has seen the message "purge is necessary" pushes the purge button, the purge operation start signal is input to the purge operation output unit 66. On the basis of the purge operation start signal, the purge operation output unit 66 operates the compressor of the purge device main body 52 and passes gas such as air to the capillary tube 56 to purge the dynamic pressure tube 12 for the predetermined fixed period, for example, for 30 seconds. While the purge is conducted, the flow sensor 2 does not measure the flow rate and also the determination circuit 50 does not operate.

After the purge, the flow rate measurement is started again, and the determination circuit 50 determines again whether or not the flow rate measurement value of the flow sensor 2 is less than the predetermined value. As a result, when the determination circuit 50 determines that the flow rate measurement value of the flow sensor 2 is less than the predetermined value, the message "purge is necessary" continues to be displayed on the display 60, the purge device main body 52 again purges the dynamic pressure tube 12 by the operator as described above. As described above, until the determination circuit 50 determines that the flow rate measurement value of the flow sensor 2 is not less than the predetermined value, the purge is repeated.

Thereafter, when the determination circuit 50 determines that the flow rate measurement value of the flow sensor 2 is not less than the predetermined value, the predetermined correlation is satisfied and the output circuit 51 stops the output of the message "purge is necessary" on the display 60. As a result, since the message "purge is necessary" disappears from the display 60, the operator determines that the purge is unnecessary and stops the purge.

In the above-described exhaust gas measuring system 100, the $CO_2$ measurement concentration is used as the index value for the operational state, and therefore it is possible to surely determine that the internal combustion engine E is under operation. This is because the exhaust gas is surely generated when the internal combustion engine E is under operation, and considerable amount of $CO_2$ is contained in the exhaust gas compared with air. Further, the exhaust gas that has passed through the catalyst CAT is introduced into the $CO_2$ sensor 28. Since $CO_2$ hardly receives an influence of the catalyst CAT, when $CO_2$ is detected, it can be determined that the exhaust gas flows surely.

Immediately after abnormality of the flow sensor 2 occurs, the processing executing circuit 48 displays the message "purge is necessary" on the display 60, and therefore the operator who has seen the display 60 immediately purges the flow sensor 2 to eliminate an abnormal state of the flow sensor 2 rapidly.

As described above, the flow sensor 2 is purged at appropriate timing, and therefore unnecessary processing such as an excessive purge operation is prevented and consumption of an on-vehicle battery is reduced.

In the exhaust gas measuring system 100 used in the road traveling test, the road traveling test may be performed for several hours. In addition, since the road traveling test may be performed only by a vehicle driver, it is difficult to always monitor all measurement data compared with a test in a test bench. In the case in which clogging etc. occur in the flow sensor 2 on the way of the above road traveling test, but the road traveling test is continued without knowing the clogging, data after troubles occur in the flow sensor 2 is wasted, as well as wasting time for travel.

In contrast with the above, according to the exhaust gas measuring system 100, it is possible to find out the abnormality of the flow sensor 2 in real time during traveling as described above and take the normalizing action. As a result, it is possible to eliminate the wasted test travel by interrupting the road traveling test on the spot and reduce invalid data during the road traveling test as much as possible by taking the normalizing action.

The present invention is not limited to the embodiment, and it goes without saying that various modifications can be performed without departing from the spirit and scope of the present invention. In the above, for example, the $CO_2$ sensor 28 is used as the operational state detecting sensor; however, the present embodiment is not limited thereto. As the operational state detecting sensor, each sensor may be used that detects a vehicle speed, an accelerator opening, a rotation speed of the internal combustion engine, an intake air flow rate of the internal combustion engine or fuel consumption of the internal combustion engine, or the intake air flow rate of the internal combustion engine and the fuel consumption of the internal combustion engine, and outputs them as an operational state signal. In particular, when the intake air flow rate of the internal combustion engine is used, variation of the operational state signal due to differences of vehicle types is small and time and labor for customization of the operational state detecting sensor due to the vehicle types are saved. Like an exhaust gas measuring system 200 illustrated in FIG. 5, the vehicle speed, the accelerator opening, the rotation speed of the internal combustion engine, the intake air flow rate of the internal combustion engine or the fuel consumption of the internal combustion engine is obtained from signals output from an ECU (Engine Control Unit) 68 or from an OBD (On-Board Diagnostics). In addition, the vehicle speed may be obtained, for example, from a GPS mounted on the vehicle other than the ECU 68 or the OBD.

Figure 5:
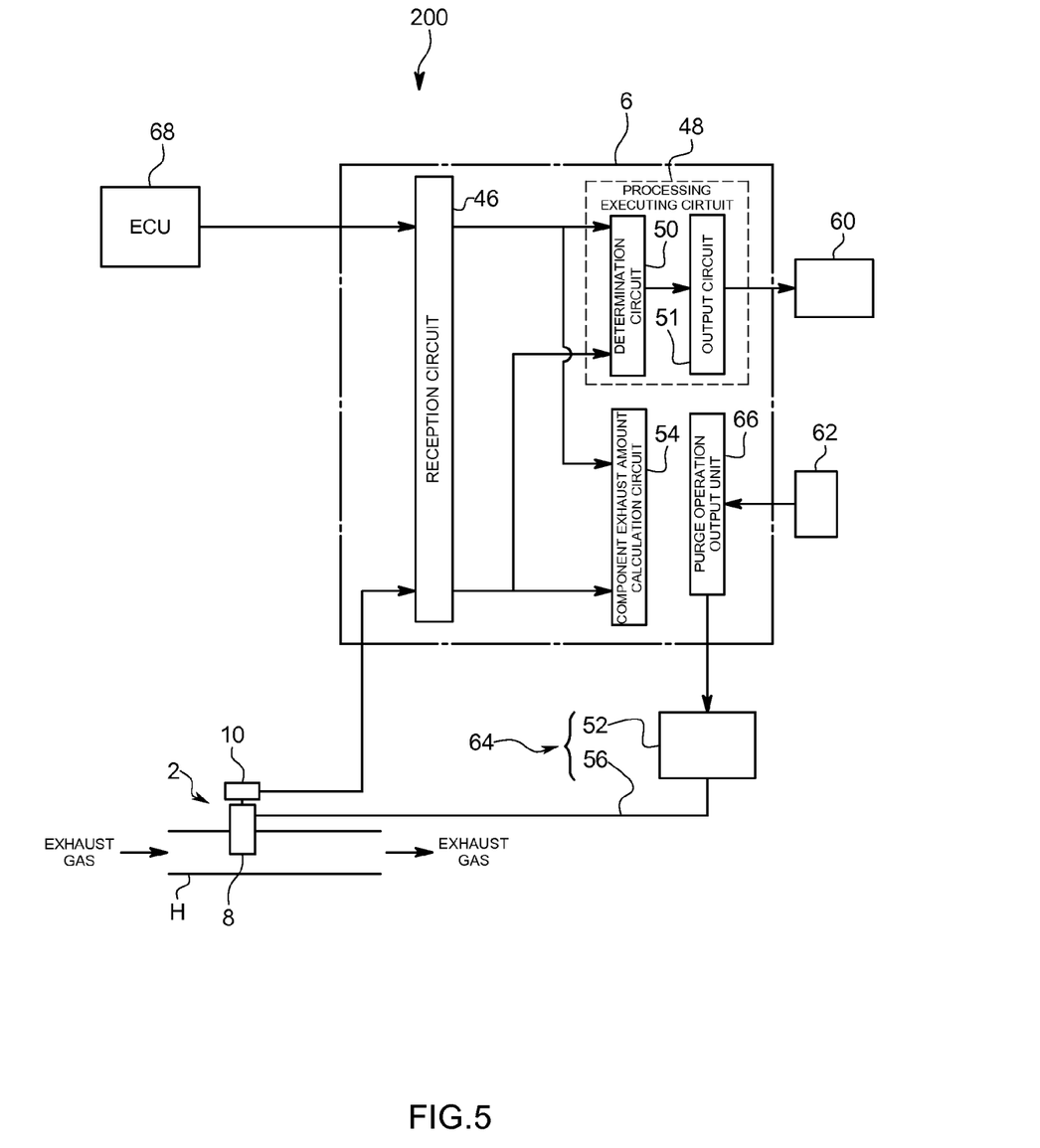
FIG. 5 is a schematic diagram illustrating a specific configuration of an exhaust gas measuring system according to another embodiment.

The reception circuit 46 receives an intake air flow rate etc. output from the ECU 68 or the OBD as the operational state signal. Thereafter, in the same manner as in one example of operations of the above-described exhaust gas measuring system 100, the determination circuit 50 determines whether or not the internal combustion engine E is under operation on the basis of the intake air flow rate etc. as the index value indicating the operational state. When the determination circuit 50 determines that the internal combustion engine E is under operation and determines that the predetermined correlation is not satisfied between the intake air flow rate etc. and the flow rate measurement value, the normalizing action of the flow sensor 2 is taken.

As each of the above-described operational state detecting sensors, an engine rotation speed sensor previously mounted on the vehicle VH, the $CO_2$ concentration meter mounted on the exhaust gas measuring system, or the like may be used. This makes it possible to simplify the configuration of the exhaust gas measuring system 100. Further, a dedicated sensor may be provided as the operational state detecting sensor.

In the above, when the internal combustion engine E is under operation, a state in which the flow rate measurement value is less than the predetermined value is determined to be a state in which the predetermined correlation is not satisfied; however, the present embodiment is not limited thereto. For example, it may be configured that the intake air flow rate is regarded as the index value for the operational state and it is determined that the predetermined correlation is not satisfied in the case that the flow rate measurement value does not increase as the index value increases but is kept for a fixed period of time to be less than a flow rate measurement value that should be indicated as the index value increases, although the flow rate measurement value should increase (for example, proportionally) according to an increase of the index value. As the case in which the intake air flow rate increases, there is a case in which the vehicle accelerates in the road traveling test.

Figure 6:
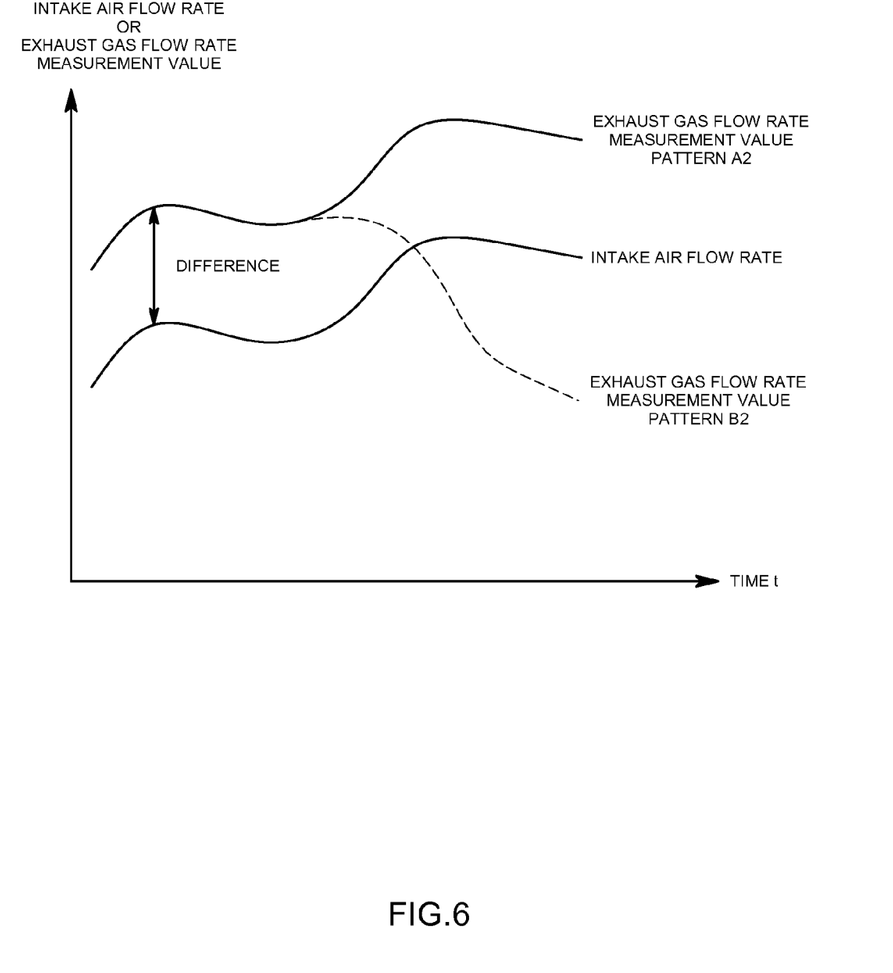
FIG. 6 is a schematic diagram illustrating various states of an intake air flow rate and the exhaust gas flow rate measurement value according to another embodiment.

Specifically, as illustrated in FIG. 6, the case in which the predetermined correlation is satisfied indicates a case in which as illustrated in an exhaust gas flow rate measurement value pattern A2, the flow rate measurement value increases while maintaining a predetermined difference accompanied by an increase and decrease in the intake air flow rate. The predetermined difference corresponds to the fuel consumption.

In contrast to the above, the case in which the predetermined correlation is not satisfied indicates that, as illustrated as pattern B2 of an exhaust gas flow rate measurement value, a state in which the flow rate measurement value decreases without maintaining the predetermined difference continues for a fixed period of time. Alternatively, compared with a ratio between the exhaust gas flow rate and the intake air flow rate when the predetermined correlation is satisfied, when the ratio is not kept within a predetermined range, it may be considered that the predetermined correlation is not satisfied.

Further, it may be configured that in the case that the intake air flow rate increases, an increased amount of the intake air flow rate for a fixed period of time, for example, for five seconds is regarded as the index value for the operational state and it is determined that the predetermined correlation is not satisfied if the flow rate measurement value measured during the fixed period of time does not increase by a fixed increased amount. A value other than the intake air flow rate may be used as the index value for the operational state. Further, even the above-described vehicle speed, accelerator opening, rotation speed of the internal combustion engine, fuel consumption of the internal combustion engine, or the like may be used similarly.

Timing at which the processing executing circuit 48 displays the message "purge is necessary" on the display 60 may be set immediately after it is found out that there is the abnormality of the flow sensor 2. Furthermore, the message may be displayed at various timing, for example, when a fixed time elapses after it is found out that there is the abnormality, i.e., after the vehicle VH slows down to a predetermined speed or the vehicle VH stops, considering security of the operator. In the case of the above-described abnormality, the timing at which the normalizing action of the flow sensor 2 is taken can be appropriately obtained in accordance with vehicle conditions during measurement of the exhaust gas or conditions of the operator.

The processing executing circuit 48 displays the message "purge is necessary" on the display 60 and the operator sees the display 60 and starts a purge operation; however, the present embodiment is not limited thereto. At the timing at which the predetermined correlation is not satisfied, the processing executing circuit 48 may output a signal for starting the purge operation to the purge operation output unit 66 and automatically purge the dynamic pressure tube 12. In this case, the component exhaust amount calculation circuit 54, the flow sensor 2, the determination circuit 50, and the like may be held in the non-operational state. Further, when a component measurement value of the component exhaust amount calculation circuit 54 or the flow rate measurement value of the flow sensor 2 is added up to perform the exhaust gas measurement, while the component measurement value or the flow rate measurement value is obtained during the purge, a purge operation start flag and a purge operation completion flag are given. In this case, the measurement values can be calculated, omitting the measurement values between the purge operation start flag and the purge operation completion flag. Further, even when the dynamic pressure tube 12 is automatically purged, the processing executing circuit 48 is preferably configured so as to measure a distance and a time in which the vehicle moves during the purge and, after completion of the purge, fill values obtained from the measured distance and time.

The flow sensor is not limited to the pitot tube type flowmeter, and a differential pressure type flowmeter, an ultrasonic flowmeter, a Karman vortex flowmeter, a hot-wire flowmeter, a laminar flowmeter, a turbine flowmeter, or the like may be used. As the flow sensor 2, even if a flowmeter of any system is used, the determination circuit 50 determines whether or not the predetermined correlation is satisfied between the index value for the operational state indicated by the operational state signal and the flow rate measurement value obtained by the flow sensor 2. The process permits the abnormality of the flow sensor 2 to be detected.

The $CO_2$ measurement concentration is used as the index value for the operational state; however, any components of the exhaust gas except $CO_2$ may be used for the index value, and the measurement concentration of $NO_X$ or HC may be used as the index value although an influence is slightly received through a catalyst. Alternatively, if it is configured that the exhaust gas before passing through the catalyst CAT is introduced into the analyzer 4, the measurement concentration of $NO_X$ or HC can be appropriately used as the index value.

Further, $O_2$ concentration may be used as the index value for the operational state. In this case, it may be determined that the internal combustion engine E is under operation when the concentration of $O_2$ in the exhaust gas is less than the $O_2$ concentration in air. It is possible to measure the $O_2$ concentration if a zirconia type $O_2$ concentration meter is disposed at an upstream side or a downstream side of the flow sensor 2, or in front of the catalyst CAT.

The message "purge is necessary" is reported to the operator by the display 60; however, the present embodiment is not limited thereto. The effect may be reported by a voice with use of a speaker, or a warning light may be emitted to report the effect.

The message is not limited to "purge is necessary" but may be "abnormality occurs" etc., which is reported by the display or the voice. Further, it is sufficient to just report the effect that troubles etc. occur in the flow sensor 2 to the operator by the display etc.

In the above, the purge device 64 purges the dynamic pressure tube 12; however, the purge device 64 may also purge the static pressure tube 14. The reason is that, for example, when the internal combustion engine E stops, the exhaust gas may flow back and foreign materials may be attached to the static pressure measuring holes 22.

The conversion circuit 10 of the flow sensor 2, and each of the calculation circuits 36, 40 and 44 of the $CO_2$ sensor 28, the $NO_X$ sensor 30 and the HC sensor 32 are arranged at each of the sensor main bodies 8, 34, 38 and 42, respectively; however, it is not limited thereto, but they may be provided in the information processing apparatus 6, or between each sensor and the information processing apparatus 6.

REFERENCE SIGNS LIST

100 Exhaust gas measuring system
VH Vehicle
2 Flow sensor
4 Analyzer
6 Information processing apparatus
8 Sensor main body
46 Reception circuit
48 Processing executing circuit
52 Purge device main body

What is claimed is:

1. An exhaust gas measuring system comprising:
   an exhaust gas measuring information processing apparatus;
   a flow sensor that measures a flow rate of exhaust gas flowing through an exhaust gas tube of an internal combustion engine and outputs a flow rate measurement signal indicating a measurement value of the flow rate; and
   an operational state detecting sensor that detects an operational state of the internal combustion engine and outputs an operational state signal indicating the detected operational state, wherein
   the exhaust gas measuring information processing apparatus includes:
   a reception circuit that receives the flow rate measurement signal indicating the flow rate measurement value of the exhaust gas flowing through the exhaust gas tube of the internal combustion engine and the operational state signal indicating the operational state of the internal combustion engine; and
   a processing executing circuit that executes predetermined processing relevant to reporting abnormality or normalizing of the flow sensor that outputs the flow rate measurement signal when a predetermined correlation is not satisfied between an index value for the operational state indicated by the operational state signal and the flow rate measurement value indicated by the flow rate measurement signal, wherein
   the flow sensor includes a sensor main body and a conversion circuit that converts an output signal from the sensor main body into the flow rate measurement signal,
   the sensor main body includes an exhaust gas introduction tube which is attached to the exhaust gas tube and into which the exhaust gas is introduced, and
   as part of the predetermined processing relevant to normalizing of the flow sensor, the processing executing circuit starts a purge operation for the exhaust gas introduction tube at the moment that the predetermined correlation is not satisfied.

2. The exhaust gas measuring system according to claim 1, wherein
   in the case that the system identifies that the internal combustion engine is under operation, on the basis of the index value, and that the flow rate measurement value is less than a predetermined value, the system determines that the predetermined correlation is not satisfied.

3. The exhaust gas measuring system according to claim 1, wherein
   as part of the predetermined processing, the processing executing circuit reports abnormality of the flow sensor.

4. The exhaust gas measuring system according to claim 1, wherein
   the operational state detecting sensor that outputs the operational state signal, detects as the index value, a rotation speed of the internal combustion engine, or an intake air flow rate of the internal combustion engine, or a fuel consumption of the internal combustion engine, or a concentration of a predetermined component contained in the exhaust gas, and
   the processing executing circuit determines that the internal combustion engine is in an operational state when the index value is more than a predetermined value.

5. The exhaust gas measuring system according to claim 1, wherein
   the operational state detecting sensor is a CO2 sensor that measures concentration of CO2 in the exhaust gas, and
   the processing executing circuit recognizes the measurement concentration of the CO2 as the index value for the operational state, and determines that the internal combustion engine is under operation in the case when the index value is more than a predetermined value.

6. An exhaust gas measuring system comprising:
   an exhaust gas measuring information processing apparatus;
   a flow sensor that measures a flow rate of exhaust gas flowing through an exhaust gas tube of an internal combustion engine and outputs a flow rate measurement signal indicating a measurement value of the flow rate;
   an operational state detecting sensor that detects an operational state of the internal combustion engine and outputs an operational state signal indicating the detected operational state; and
   a concentration measuring sensor that measures a concentration of a predetermined component in the exhaust gas, wherein
   the exhaust gas measuring information processing apparatus includes:
   a reception circuit that receives the flow rate measurement signal indicating the flow rate measurement value of the exhaust gas flowing through the exhaust gas tube of the internal combustion engine and the operational state signal indicating the operational state of the internal combustion engine;
   a processing executing circuit that executes predetermined processing relevant to reporting abnormality or normalizing of the flow sensor that outputs the flow rate measurement signal when a predetermined correlation is not satisfied between an index value for the operational state indicated by the operational state signal and the flow rate measurement value indicated by the flow rate measurement signal; and
   a component exhaust amount calculation circuit that calculates an exhaust amount of the predetermined component on a basis of a product of measurement concentration of the predetermined component measured by the concentration measuring sensor and the flow rate measurement value measured by the flow sensor, wherein
   the system is a vehicle-mounted type exhaust gas measuring system.

7. The exhaust gas measuring system according to claim 6, wherein
   in the case that the system identifies that the internal combustion engine is under operation, on the basis of the index value, and that the flow rate measurement value is less than a predetermined value, the system determines that the predetermined correlation is not satisfied.

8. The exhaust gas measuring system according to claim 6, wherein
   as part of the predetermined processing, the processing executing circuit reports abnormality of the flow sensor.

9. The exhaust gas measuring system according to claim 6, wherein
   the operational state detecting sensor that outputs the operational state signal, detects as the index value, a rotation speed of the internal combustion engine, or an intake air flow rate of the internal combustion engine, or a fuel consumption of the internal combustion engine, or a concentration of a predetermined component contained in the exhaust gas, and the processing executing circuit determines that the internal combustion engine is in an operational state when the index value is more than a predetermined value.

10. The exhaust gas measuring system according to claim 6, wherein the operational state detecting sensor is a CO2 sensor that measures concentration of CO2 in the exhaust gas, and the processing executing circuit recognizes the measurement concentration of the CO2 as the index value for the operational state, and determines that the internal combustion engine is under operation in the case when the index value is more than a predetermined value.

11. An exhaust gas measuring method using a vehicle-mounted type exhaust gas measuring system including an exhaust gas measuring information processing apparatus, a flow sensor that measures a flow rate of exhaust gas flowing through an exhaust gas tube of an internal combustion engine and outputs a flow rate measurement signal indicating a measurement value of the flow rate, an operational state detecting sensor that detects an operational state of the internal combustion engine and outputs an operational state signal indicating the detected operational state, and a concentration measuring sensor that measures concentration of a predetermined component in the exhaust gas comprising:

receiving the flow rate measurement signal indicating the flow rate measurement value of the exhaust gas flowing through the exhaust gas tube of the internal combustion engine and the operational state signal indicating the operational state of the internal combustion engine;

executing predetermined processing relevant to reporting abnormality or normalizing of the flow sensor that outputs the flow rate measurement signal when a predetermined correlation is not satisfied between an index value for the operational state indicated by the operational state signal and the flow rate measurement value indicated by the flow rate measurement signal; and calculating an exhaust amount of the predetermined component on a basis of a product of measurement concentration of the predetermined component measured by the concentration measuring sensor and the flow rate measurement value measured by the flow sensor.

* * * * *